(12) United States Patent
Schade et al.

(10) Patent No.: US 12,372,522 B2
(45) Date of Patent: Jul. 29, 2025

(54) OPTICAL SENSOR, SYSTEM AND METHOD FOR DETECTING PATHOGENIC GERMS

(71) Applicant: FRAUNHOFER-GESELLSCHAFT ZUR FÖRDERUNG DER ANGEWANDTEN FORSCHUNG E.V., Munich (DE)

(72) Inventors: Wolfgang Schade, Freiburg (DE); Eike Hübner, Freiburg (DE); Vladislav Reimer, Freiburg (DE)

(73) Assignee: Fraunhofer-Gesellschaft zur Förderung der angewandten Forschung e.V., Munich (DE)

( * ) Notice: Subject to any disclaimer, the term of this patent is extended or adjusted under 35 U.S.C. 154(b) by 621 days.

(21) Appl. No.: 17/471,696

(22) Filed: Sep. 10, 2021

(65) Prior Publication Data
US 2022/0082558 A1 Mar. 17, 2022

(30) Foreign Application Priority Data
Sep. 11, 2020 (DE) .......................... 102020123800.2

(51) Int. Cl.
*G01N 33/543* (2006.01)
*G01N 33/569* (2006.01)

(52) U.S. Cl.
CPC ..... *G01N 33/54373* (2013.01); *G01N 33/569* (2013.01)

(58) Field of Classification Search
CPC ............. G01N 21/774; G01N 21/7743; G01N 33/54373; G01N 33/569; G01N 21/7703
See application file for complete search history.

(56) References Cited

U.S. PATENT DOCUMENTS

| 2005/0135723 A1* | 6/2005 | Carr ..................... G01N 33/569 385/12 |
| 2005/0175273 A1 | 8/2005 | Iida et al. |

(Continued)

FOREIGN PATENT DOCUMENTS

| DE | 102004015906 | 11/2005 |
| DE | 102010036082 | 3/2012 |

(Continued)

OTHER PUBLICATIONS

European Search Report issued Feb. 9, 2022, in EP Patent Application No. 21195963.0.

*Primary Examiner* — Jonathan M Hurst
(74) *Attorney, Agent, or Firm* — Womble Bond Dickinson (US) LLP

(57) ABSTRACT

An optical sensor has a substrate with first and second sides, one side being provided with first and second waveguides. The first and second waveguides have respective first and second measuring points along their respective lengths, each measuring point includes at least one interruption. The first measuring point, which belongs to the first waveguide, is functionalized by at least one coating while the second measuring point, which belongs to the second waveguide, is not functionalized by that same coating. The functionalized coating may include a substance (e.g., antibody) which corresponds to a pathogenic germ. A light source may simultaneously direct light into both waveguides and a light detector may simultaneously detect light signals exiting the waveguides. Differences in light intensities of the received light signals at one or more wavelengths, may reveal the presence of a pathogenic germ in a liquid sample applied to the first and second measurement points.

21 Claims, 4 Drawing Sheets

(56) References Cited

U.S. PATENT DOCUMENTS

2009/0244532 A1* 10/2009 Letant .................. G01N 21/774
                                                          356/244
2018/0017495 A1    1/2018  Bremer et al.

FOREIGN PATENT DOCUMENTS

DE      102018118110       1/2020
EP         1 509 593 B1    8/2007

* cited by examiner

OPTICAL SENSOR, SYSTEM AND METHOD FOR DETECTING PATHOGENIC GERMS

CROSS-REFERENCE TO RELATED APPLICATIONS

This application claims priority under 35 USC § 119 to German Patent Application No. 10 2020 123 800.2, filed Sep. 11, 2020. The contents of the aforementioned application are incorporated by reference in their entirety.

FIELD OF THE INVENTION

The subject matter of the present application relates to an optical sensors configured to detect pathogenic germs, such as microorganisms or subcellular pathogens, e.g. algae, bacteria, parasites, fungi or viruses. It is more specifically directed to such sensors which can be used in conjunction with cell phones or tablet computers to perform such detection.

SUMMARY OF THE INVENTION

In one aspect, the subject matter of the present application is directed to an optical sensor having a substrate with first and second sides, one side being provided with first and second waveguides. The first and second waveguides have respective first and second measuring points along their respective lengths, each measuring point comprising at least one interruption. The first measuring point, which belongs to the first waveguide, is functionalized by at least one coating. However, the second measuring point, which belongs to the second waveguide, is not functionalized by said at least one coating.

A light source may simultaneously direct light into both waveguides and a light detector may simultaneously detect light signals exiting the waveguides. Differences in light intensities of the received light signals at one or more wavelengths, may reveal the presence of a pathogenic germ in a liquid sample applied to the first and second measurement points.

A system may include the aforementioned sensor coupled to either a cell phone or a table computer. The cell phone or tablet computer comprises a camera and a light source. An adaptor is mounted on the cell phone or tablet computer, and the sensor is mounted to the adaptor such that first ends of the first and second waveguides are opposed to the light source, and second ends of the first and second waveguides are opposed to the camera. The cell phone or tablet computer is provisioned with a software application configured to control the light source and the camera, and process the received light signals to determine whether a particular pathogenic germ is present.

Thus, the invention relates to an optical sensor comprising a substrate having at least a first side and an opposite second side, wherein at least a first waveguide is arranged at least on the first side. The invention relates further to a method for detecting pathogenic germs, in which a liquid sample is applied to an aforementioned sensor and an optical signal is coupled into the first end of the waveguide. Devices and methods of this type can be used for the detection of pathogenic germs that cause diseases in other organisms. Microorganisms or subcellular pathogens, e.g. algae, bacteria, parasites, fungi or viruses, are hereinafter referred to as pathogenic germs.

According to the invention, an optical sensor in the form of an integrated optical component is disclosed. The sensor comprises a substrate. In some embodiments, the substrate may be made from a polymer. In other embodiment, the substrate may comprise a polymer. A polymer may be selected from polycarbonate or cycloolefin copolymers (COC) in some embodiments. Alternatively, the substrate can also comprise, or consist of, glass, quartz or a semiconductor material. A semiconductor material can be selected from germanium, silicon, a group-III-V compound semiconductor, or diamond. The substrate can have a multilayer structure, e.g. a first polymer layer applied to glass, a second polymer, or a semiconductor.

The substrate can have a thickness of about 50 µm to about 250 µm or of about 80 µm to about 150 µm or of about 750 µm to about 1250 µm. The substrate can have a polygonal or circular basic shape. In particular, the substrate can be rectangular and have a length and a width of about 1 cm to about 5 cm or of about 0.5 cm to about 3 cm in each case. The substrate has a first side and an opposite second side, the first and the second side each being the largest surfaces of the substrate. The first side and the opposite second side are connected to each other by lateral surfaces formed on lateral edges of the substrate.

At least a first waveguide is arranged at least on the second side of the substrate. The waveguide can be generated e.g. by UV lithography. In some embodiments of the invention, the waveguide can be obtained in that the substrate is at least partially coated, e.g. in a sol-gel process, a vacuum deposition method, or a spin-coating method. The layer produced in this way can have a refractive index which differs from that of the substrate, and can subsequently be partially removed by masking with a photoresist, exposing, developing and etching so that a waveguide is created on the surface of the substrate. In other embodiments of the invention, a homogeneous substrate can be partially removed by masking with a photoresist, exposing, developing, and etching so that a waveguide is exposed on the second side of the substrate.

In some embodiments, the waveguide can have a height of about 1 µm to about 50 µm or of about 2 µm to about 6 µm or of about 35 µm to about 45 µm and/or a width of about 1 µm to about 1000 µm or of about 10 µm to about 125 µm or of about 10 µm to about 50 µm or of about 80 µm to about 120 µm or of about 1 µm to about 10 µm or of about 500 µm to about 1000 µm.

The waveguide can have a first end and an opposing second end. Both the first end and the second end of the waveguide can be arranged on (i.e., "terminate at") an edge (the same edge) of the substrate. In other embodiments of the invention, the first end and the second end of the waveguide can be arranged on (i.e., "terminate at") two different edges of the substrate.

The waveguide also comprises at least a first measuring point. At the measuring point, the waveguide has at least one interruption. In other embodiments of the invention, the number of interruptions of the waveguide can be greater than one and can be, for example, between about 3 and about 60 interruptions or between about 10 and about 30 interruptions, or between about 5 and about 20 interruptions or between about 50 and about 100 interruptions. Between two adjacent interruptions of the waveguide there is, in turn, a comparatively short waveguide element, the length of which corresponds approximately to the length of the interruption. In other embodiments of the invention, the waveguide between two adjacent interruptions can be larger than the interruptions by a factor between about 2 and about 20, or by a factor between 1 and 10.

When the optical sensor is operated, an optical signal is coupled in at the first end of the waveguide and is detected at the second end of the waveguide by means of a detector. At the interruptions, some of the coupled-in light is reflected so that the transmitted intensity detected in the detector is less than the coupled-in intensity. If there is a liquid, in particular aqueous, medium at the measuring point, the difference in refractive index between the material of the waveguide and the liquid medium is reduced, as a result of which the power transmitted through the waveguide increases. If the liquid medium comprises pathogenic germs, these particles act as scattering centers, which scatter some of the coupled-in light out of the waveguide. This causes the intensity detected in the detector to decrease again, as a result of which it is possible to detect the presence of the particles and their number.

In some embodiments of the invention, the optical signal coupled into the first waveguide is selected in such a way that at least some of the spectrum has a wavelength which is greater than or at least equal to the diameter of the particles to be detected. In some embodiments of the invention, the wavelength can be larger than the particles to be detected by a factor of about 4 to a factor of about 7. In some embodiments of the invention, the light source can be, or comprise, an LED, a superluminescent diode or a semiconductor laser. In some embodiments of the invention, the optical signal can be monochromatic. In other embodiments of the invention, the optical signal can include a plurality of different wavelengths or a plurality of wavelength ranges, or be a white light source.

The detector coupled to the second end of the first waveguide can be a generally known photodiode or a photodiode array. In some embodiments of the invention, the detector can comprise a spectrometer, in particular a micro-optical spectrometer or an Arrayed Waveguide Grating (AWG). Such elements can optionally be integrated on the substrate. In some embodiments of the invention, the detector can be a CCD or a CMOS detector, which can be designed as a line detector or an area detector. Such a line or area detector can comprise a plurality of pixels and thus allow a spatial resolution. Individual pixels can be subdivided into subpixels and in this way allow a detection of different wavelengths or different wavelength ranges. Therefore, a detector of this type can be a camera chip known per se.

In some embodiments of the invention, the interruptions of the first waveguide can be arranged periodically in the first measuring point. In some embodiments of the invention, the interruptions of the first waveguide in the first measuring point can have a length of about 2 μm to about 20 μm, or a length of about 3 μm to about 10 μm or a length of about 2 μm to about 6 μm. Said dimensions allow a reliable attachment of the particles or pathogenic germs to be detected and a favorable signal-to-noise ratio.

In some embodiments of the invention, one coupler each can be arranged on the first end of the waveguide and/or on the opposite second end of the waveguide. In some embodiments, a coupler of this type can be selected from a grating coupler or a light funnel or taper. This can increase the efficiency of the coupling-in or coupling-out between light source and detector so that the detection limit and/or the measurement accuracy can be improved.

In some embodiments of the invention, the first measuring point can be functionalized by at least one coating. A functionalization of this type allows the selective coupling of predeterminable microorganisms or subcellular pathogens so that a specific detection of certain pathogenic germs is made possible without other germs and/or inorganic particles influencing the measurement accuracy.

In some embodiments, the coating can comprise, or consist of, a multilayer system which comprises a first layer that comprises Al2O3 and has a layer thickness of about 10 nm to about 50 nm. In some embodiments of the invention, this layer can be produced by applying an aluminum coating e.g. by a sputtering process or by a thermal vapor deposition method, which coating is subsequently exposed to a plasma while adding oxygen so that the aluminum layer is oxidized to give $Al_2O_3$.

In some embodiments of the invention, a silane can be bonded to this layer, which offers binding sites for biological molecules. In some embodiments of the invention, (3-glycidyloxypropyl)-trimethoxysilane can be attached to the terminal Al—OH group of the $Al_2O_3$ layer. In the final step of the functionalization, antibodies can be attached for the selective bonding of the viruses to be detected via a reaction of their amino groups with the epoxy functionality of the immobilized silane. The viruses bound to the antibodies then act as scattering centers on the surfaces of the first measuring point of the first waveguide.

In some embodiments of the invention, the sensor can also comprise a second waveguide which has at least a second measuring point which comprises at least one interruption of the second waveguide. In some embodiments of the invention, the second measuring point may not be functionalized by at least one coating as described above in connection with the first measuring point. The geometrical structure of the first and the second measuring points can be identical in some embodiments of the invention. In this way, the second waveguide can be used to generate a reference signal so that the accuracy of the measuring method can be increased due to the differential measurement of the light intensity exiting the two waveguides.

In some embodiments of the invention, the sensor can also comprise a third waveguide which has a first end and an opposing second end. The second end can be arranged adjacent to the second end of the first and/or second waveguide in the substrate, such that the optical signals guided in the third waveguide can also be detected by means of an optical detector or a subarea of a spatially resolving detector. The first end of the third waveguide can be led to the first measuring point so that scattered light from the first measuring point is coupled into the third waveguide. The presence of the particles to be detected is thus reflected by a weakening of the optical signal in the first waveguide and an increase in the optical signal in the third waveguide.

In some embodiments of the invention, the sensor can also comprise a fourth waveguide which has a first end and an opposite second end. The second end can be arranged adjacent to the second end of the first and/or second and/or third waveguide in the substrate, such that the optical signals guided in the fourth waveguide can also be detected by means of an optical detector or a subarea of a spatially resolving detector. The first end of the fourth waveguide can be led to the second measuring point so that scattered light from the second measuring point is coupled into the fourth waveguide.

The sensor proposed according to the invention and the method proposed according to the invention are particularly suitable for detecting pathogenic germs in liquid samples. In some embodiments of the invention, the application of the liquid sample to the first and/or second measuring point can comprise the following steps: Applying the liquid sample to the measuring point, waiting for a predeterminable period of time, washing off the liquid sample with a solvent, and applying a reference liquid at least to the first measuring point and/or to the second measuring point. In some embodiments of the invention, the predeterminable period of time can be between about 1 minute and about 10 minutes or between about 3 minutes and about 5 minutes. In some embodiments of the invention, the solvent used to wash off the liquid sample can be distilled water or isotonic saline solution or a phosphate buffered saline solution (PBS). A PBS not only maintains the salt content but also the pH-value within predeterminable limit values. If the liquid sample comprises a lipid phase, hydrocarbons can also be used to wash off the liquid sample. In some embodiments of the invention, the reference liquid can be identical to the solvent used to wash off the liquid sample and can comprise, or consist of, e.g. isotonic saline solution, another salt solution, a phosphate buffered saline solution (PBS), or distilled water. The liquid sample can be selected from saliva, blood, cerebrospinal fluid, sweat, urine or other body fluids which can comprise pathogenic germs to be detected.

During the exposure of the liquid sample to the measuring points, pathogenic germs can be bound to the antibodies of the functionalized surfaces, as described above. When the liquid sample is washed off with the solvent, excess sample material is removed. The pathogenic germs adhering to the functionalized surface, however, remain in the first measuring point. The application of a reference liquid with a predeterminable refractive index is used to guide the light in a low-loss fashion through the interruptions of the measuring points so that the difference in the measured intensities at the second end of the waveguide can be used to determine the proportion of scattered light and thus the concentration of the pathogenic germs at the first measuring point.

In some embodiments of the invention, a single light source can be present which generates the optical signal that is coupled into both the first and second waveguides. This eliminates intensity variations on account of different properties of different light sources so that the light intensity in both waveguides is identical. As a result, it is possible to obtain a reliable reference signal.

In some embodiments of the invention, the sensor according to the invention can be read out with a cell phone. A light emitting diode, superluminescent diode or laser diode arranged in the cell phone can be used as a light source and the camera in the cell phone can be used as a detector. In order to mechanically attach the sensor according to the invention to the cell phone and in order to reproducibly position the first and second ends of the waveguides in front of the light source and the camera, the cell phone can be provided with an attachment which is attached to the cell phone in an interlocking manner and, in turn, accommodates the sensor in an interlocking manner.

BRIEF DESCRIPTION OF THE DRAWINGS

The embodiments may be better understood with reference to the following drawings and description. The components in the figures are not necessarily to scale. Moreover, in the figures, like-referenced numerals designate corresponding parts throughout the different views.

DETAILED DESCRIPTION

Figure 1:
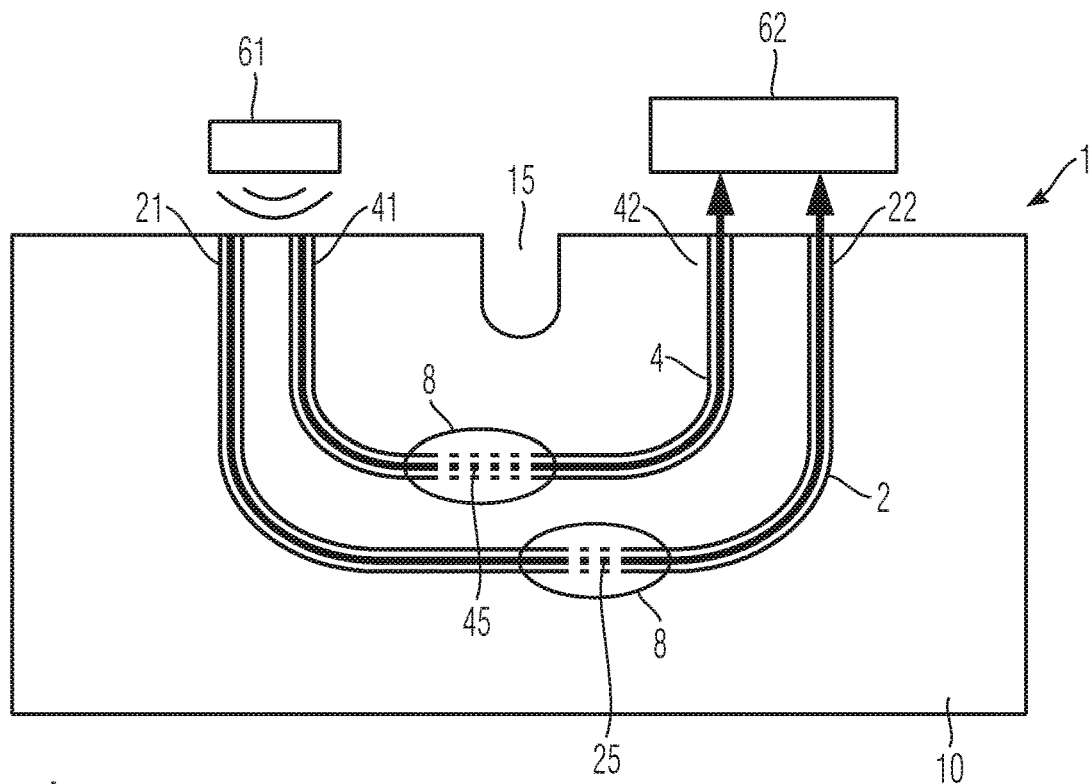
FIG. 1 shows a top view of an exemplary embodiment of a sensor according to the invention.
Figure 2:
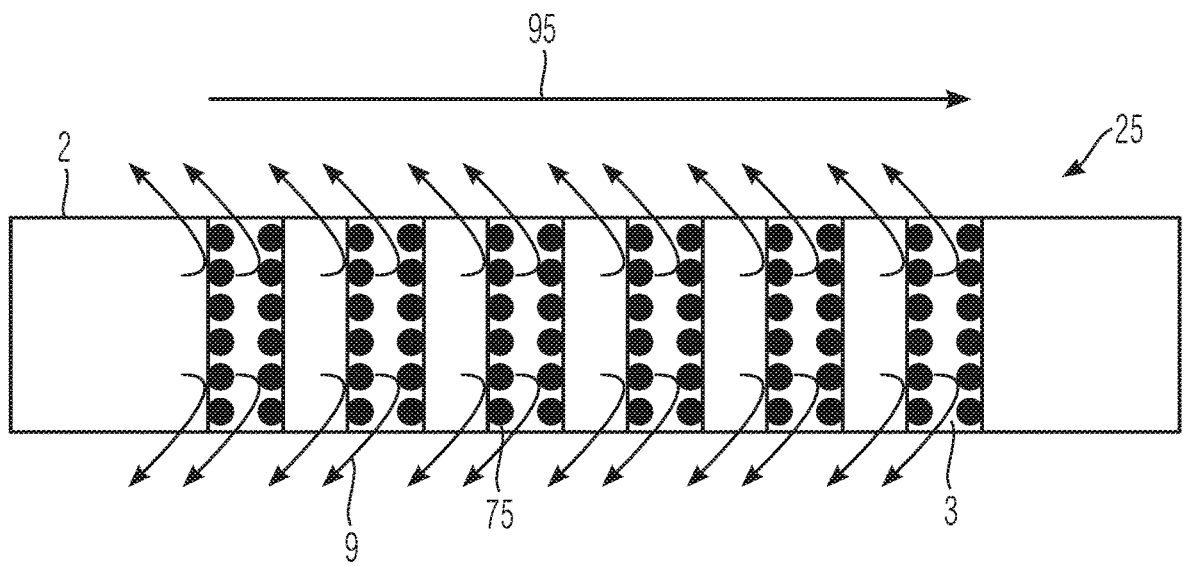
FIG. 2 shows an enlarged top view of the first measuring point.

As seen in FIGS. 1 and 2, the sensor 1 comprises a substrate 10, which in the illustrated exemplary embodiment, includes a rectangular basic shape having in each case a length and a width of about 0.5 cm to about 3 cm. The substrate has a notch 15 in order to reproducibly position the substrate when it is inserted into a reading device or a housing. By photolithographic methods, e.g., UV lithography, a first waveguide 2 and a second waveguide 4 are formed on the substrate 10. The first waveguide 2 comprises a first measuring point 25, and the second waveguide 4 comprises a second measuring point 45. The first waveguide 2 has a first end 21. The second waveguide 4 has a first end 41. Both waveguides have an opposite second end 22 and 42, respectively. As best seen in FIG. 1, the first ends 21, 41 and the second ends 22, 42 are arranged on (i.e., "terminate at") an edge of the substrate 10.

For the operation of the sensor, the first ends are coupled to a light source 61, which is a white light source, e.g., a superluminescent diode, in the illustrated exemplary embodiment. In other exemplary embodiments, the light source can also emit monochromatic light and can comprise, for example, a semiconductor laser. The first ends 21 and 41 of the first and second waveguides 2 and 4 are guided within the substrate 10 in such a narrow way that the light from a single light source 61 can be coupled into both waveguides. As a result, the intensity coupled into both waveguides can be identical and temporal fluctuations of the light intensity affect both waveguides.

The second ends 22 and 42 of the waveguides 2 and 4 are coupled to a detector 62. The detector 62 can be a two-dimensional CCD chip, for example. It comprises a plurality of pixels which allow a spatially resolved detection of incoming light. As a result, it is possible to distinguish at the detector 62 which light intensity from each of the waveguides 4 and 2 reaches the detector 62. In other embodiments of the invention, the detector 62 can be a photodiode or a photodiode array or another photoelectric transducer known per se. Therefore, the light arriving from the second waveguide 4 can be used as a reference signal and the light coming from the first waveguide 2 can be used as a measurement signal. Due to the differential evaluation of the measurement signal it is thus possible to increase the measurement accuracy.

Furthermore, each pixel of the detector 62 can comprise a plurality of subpixels so that the detector 62 is selective for different wavelengths or wavelength ranges. For example, the detector 62 can detect the intensity of red, green, and blue light separately from one another.

Figure 3:
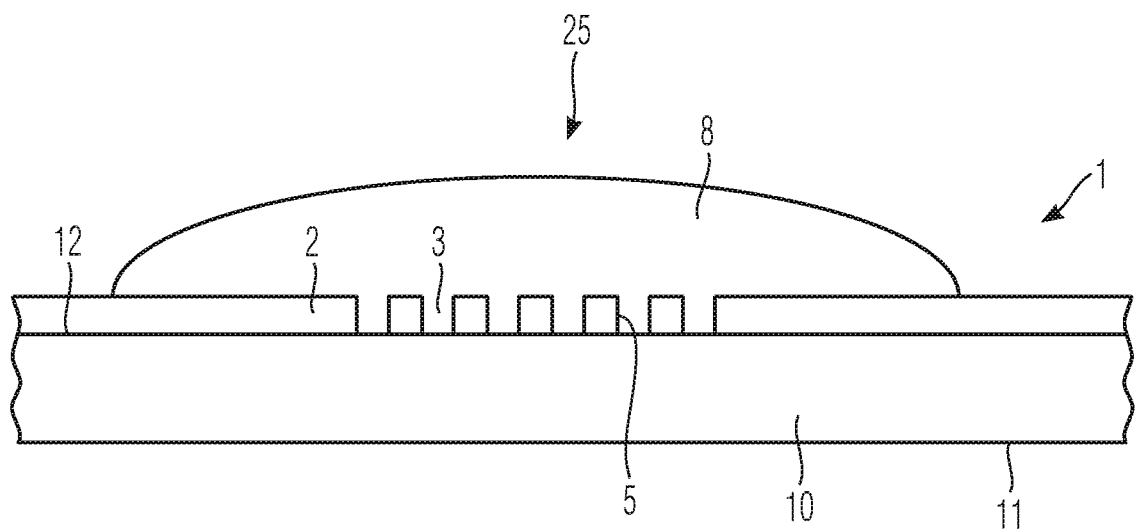
FIG. 3 shows a side view of a section of the first measuring point.
Figure 4:
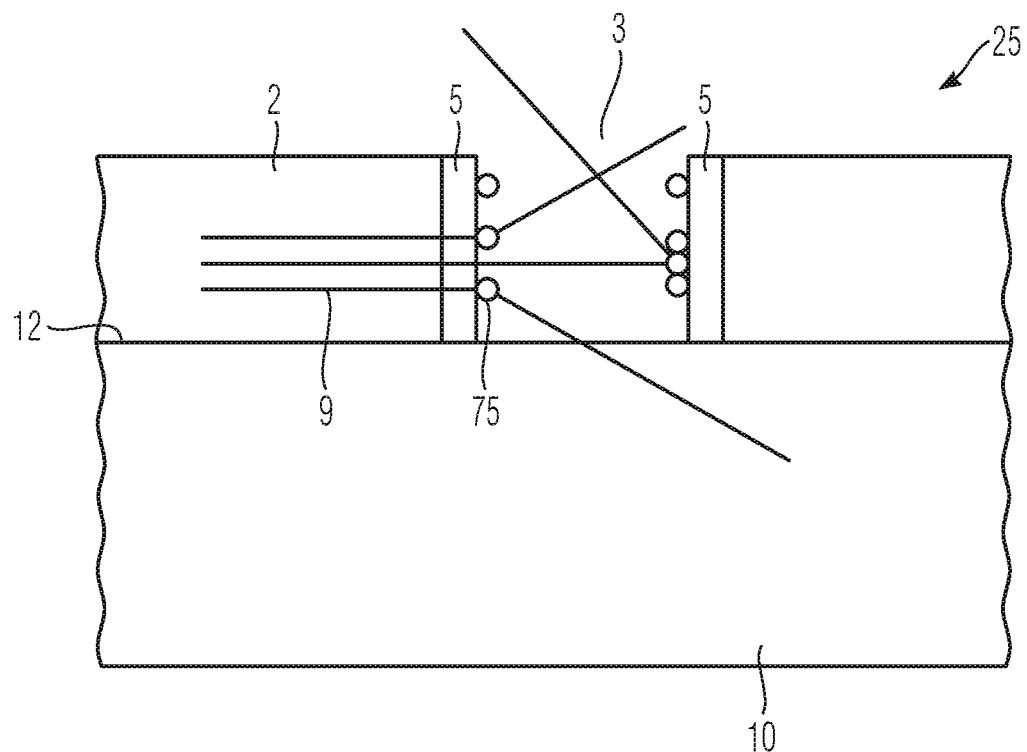
FIG. 4 shows an enlarged view of a portion of FIG. 3.

As is clear from FIGS. 3 and 4, the substrate 10 has a first side 11 and an opposite second side 12. On the second side 12, the waveguides 2 and 4 were produced by applying a liquid layer by means of spin-coating, UV-lithographic curing of the waveguide structure, and washing off the uncured areas. As a result, the waveguide 2 on the surface of the substrate 10 is produced in such a way that it is formed in a raised manner as a ridge waveguide on the second side 12 of the substrate 10. For example, the waveguide 2 can have a width of about 100 μm and a height of about 5 μm.

The first measuring point 25 of the first waveguide 2 comprises a plurality of interruptions 3. The interruptions 3 can have e.g. a length, measured in the longitudinal direction 95 of the waveguide, of about 3 µm to about 5 µm.

The material of the two waveguides 2 and 4 can have a refractive index between about 1.4 and about 1.8 or between about 1.4 and about 1.6. For this purpose, the waveguides 2 and 4 and/or the substrate 10 can, for example, consist or comprise of glass or a plastic material, e.g. of polycarbonate or epoxy resin.

FIG. 1 and FIG. 3 also show that a reference liquid 8, which fills the interruptions 3, is applied to the first measuring point 25. The reference liquid 8 can be, for example, distilled water and have a refractive index of 1.3. The liquid penetrating the interruptions 3 reduces the refractive index difference between the waveguide 2 and the interruption 3 so that a higher light intensity is measured at the detector 62 when the liquid 2 is present at the first measuring point 25. The same applies to the second measuring point 45 in the second waveguide 4.

FIG. 4 shows an enlarged section of the first measuring point 25. What is shown is a single interruption 3 from the plurality of interruptions which are present at the first measuring point 25.

As is clear from FIG. 4, at least the end faces of the waveguide 2, which border on the interruption, are provided with a coating 5. In some embodiments of the invention, the surface of the waveguide 2 can also be completely coated. The coating 5 functionalizes the surface to the effect that the pathogenic germs 75 to be detected, for example viruses, are bound to the surface. Other particles, e.g. inorganic particles or other germs, which shall not be detected, do not adhere to the coating 5. In some embodiments of the invention, the coating 5 can comprise for this purpose a multilayer system which binds selective antibodies with high adhesion to the surface of the waveguide 2 at least in the interruption 3.

The second measuring point 45 in the second waveguide 4 has a fundamentally similar or even identical design as the first measuring point 25 but does not comprise a coating 5 or at least no functionalization.

In order to carry out a measurement, a liquid sample is applied both to the first measuring point 25 and the second measuring point 45. This sample can be e.g. saliva, cerebrospinal fluid, blood, any other body fluid or also a sample obtained from a surface of an inanimate object. After a predeterminable period of time, which can be between about 1 minute and about 5 minutes, the two measuring points 25 and 45 are cleaned by means of a solvent. The solvent can be e.g. distilled water, a buffered saline solution, or another solvent which is not explicitly mentioned here. The solvent is designed and intended to wash off the residues of the liquid sample from the measuring points 25 and 45.

If pathogenic germs 75 were present in the liquid sample, they adhere to the antibodies of the coating 5 of the first measuring point 25. Since the second measuring point 45 is not functionalized, the pathogenic germs do not adhere to this point. They are rather washed off with the solvent.

A reference liquid 8 is subsequently applied to both measuring points and can comprise water or an aqueous solution, for example.

Finally, an optical signal is coupled into the first waveguide 2 and the second waveguide 4. The second optical signal in the second waveguide 4 is weakened by the interruptions 3 at the second measuring point 45 and reaches the detector 62 as a reference signal. The first optical signal in the first waveguide 2 is subject to the identical attenuation. As is clear from FIG. 2 and FIG. 4, the optical signal 9 is additionally scattered by the pathogenic germs adhering to the coating 5. The scattered light leaves the waveguide 2 so that there is an additional attenuation of the optical signal in the detector 62 when pathogenic germs are present. In this way, it is possible to detect e.g. viruses having a typical diameter of about 100 nm to about 150 nm and a typical refractive index of about 1.4 to about 1.6. When the reference signal from the second waveguide 4 is compared with the measurement signal from the first waveguide 2, the presence and concentration of the pathogenic germs 75 can thus be detected.

The sensor 1 according to the invention is characterized in that the readout can be carried out with little equipment. For example, a cell phone or a tablet computer with built-in light source and built-in camera can be used for signal acquisition and signal processing.

Figure 5:
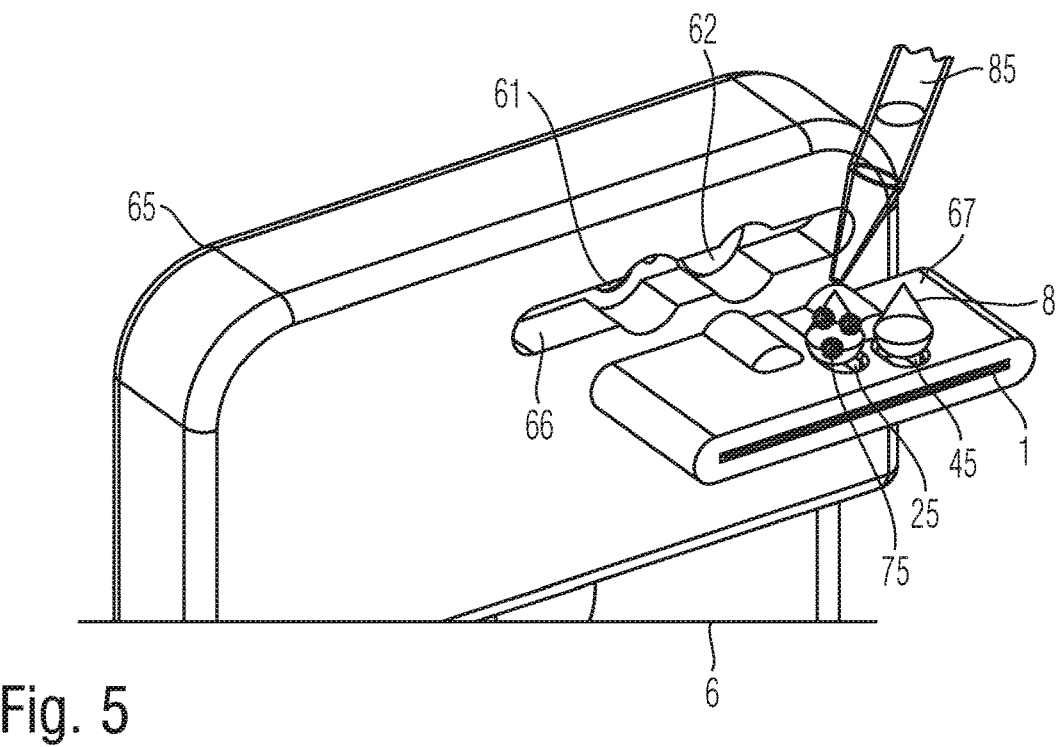
FIG. 5 shows a cell phone having a sensor according to the invention.

As shown in FIG. 5, a cell phone 6 can be provided with a fitting piece 65 (adaptor). The fitting piece 65 can be attached in interlocking manner to the cell phone 6 where it is fastened by clamping or bonding. The fitting piece 65 comprises a recess 66 which is shaped complementary to a housing 67 of the sensor 1. In other words, the fitting piece 65 is shaped and sized to receive the sensor housing 67 in the recess 66. Furthermore, the recess 66 is shaped in such a way that, when the sensor housing 67 is inserted into the recess 66, the second ends 22 and 42 of the waveguides 2 and 4 are opposed to the camera lens, as a result of which the camera is usable as a detector 62. In addition, the recess 66 is shaped in such a way that the first ends 21 and 41 of the waveguides 2 and 4 are opposite the light source 61 already present in the cell phone anyway so that the cell phone can also be used to generate the optical signal 9.

As is clear from FIG. 5, the sensor 1 is inserted in a sensor housing 67, which has two recesses so that the first measuring point 25 and the second measuring point 45 are exposed to the environment through associated holes in the housing. Furthermore, the housing 67 has coupling elements which allow the positioning of the first end 21 of the first waveguide 2 and of the first end 41 of the second waveguide 4 in front of the light source 61. In the same way, the second ends 22 and 42 of the waveguides 2 and 4 are positioned in front of the camera lens of the cell phone 6, which is used as a detector 62. Due to the shape of the recess 66 and the complementary shape of the housing 67, incorrect insertion of the housing 67 can be prevented by interlocking connection.

In order to carry out the measurement, the liquid sample is applied to the two measuring points 25 and 45 by means of a pipette 85. After sufficient contact time of the pathogenic germs 75 with the coating 5, the measuring points 25 and 45 can be washed off and the measurement can be carried out as described above. The cell phone used for readout can take over the control of the measurement process, the signal readout and the storage of the measurement data and, if necessary, also the transfer of the measurement data to a central computer. For this purpose, a corresponding computer program (an application) can be executed on the cell phone 6, which program carries out at least sub-steps of the measurement method according to the invention while the program is running on the microprocessor of the cell phone. The sensor 1 with the housing 67 can be disposed of as a disposable product after carrying out the measurement. Thus, the sensor 1 is a single-use sensor.

Figure 6:
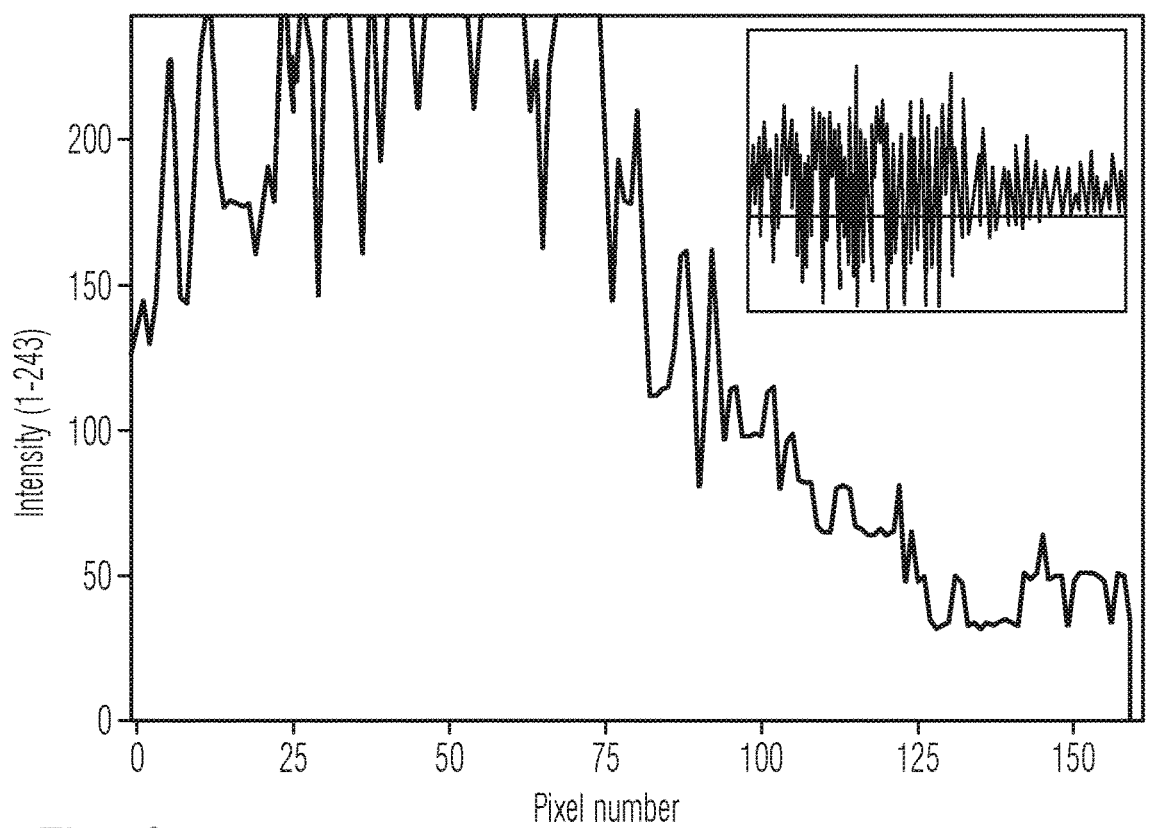
FIG. 6 shows a reference signal of a sensor according to the invention.
Figure 7:
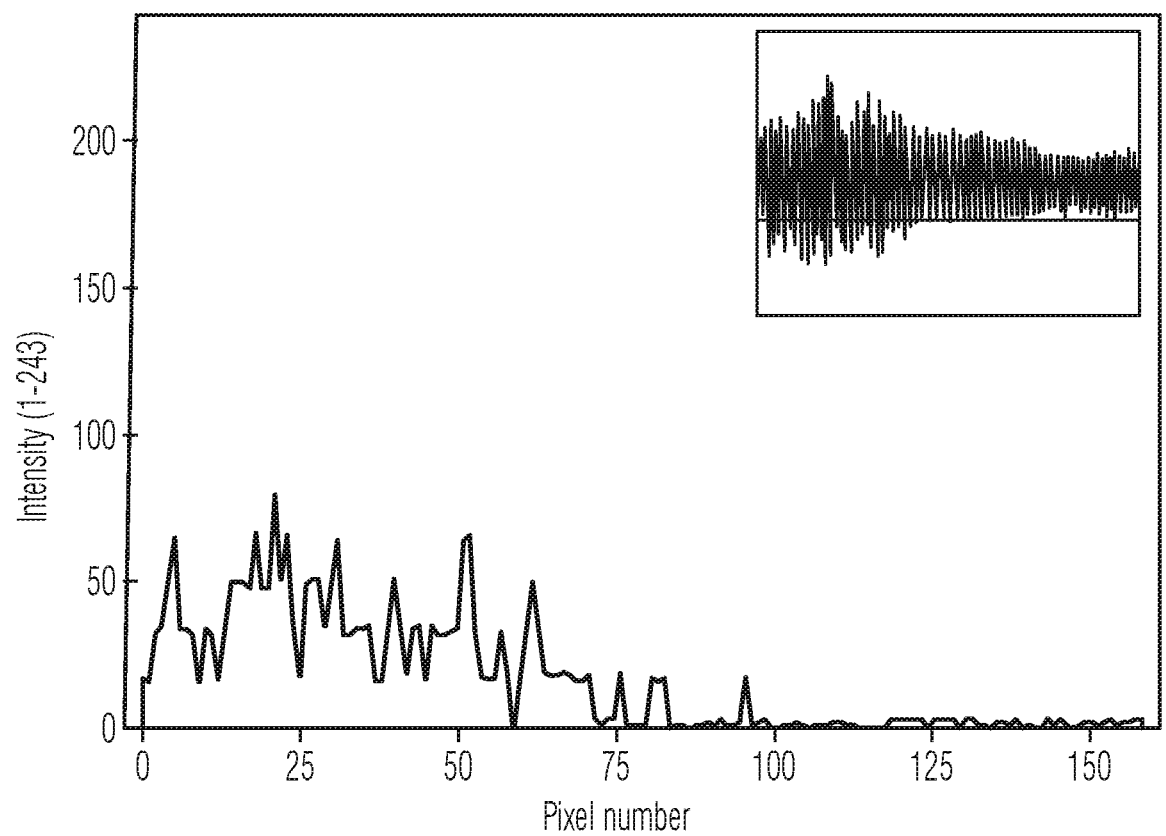
FIG. 7 shows a measurement signal of a sensor according to the invention.

FIGS. 6 and 7 illustrate once again how a measurement according to the invention is carried out. FIG. 6 shows the reference signal obtained from the second waveguide 4, and FIG. 7 depicts the measurement signal generated in the first waveguide 2.

The light source 61 generates laser light with a wavelength of 650 nm. The employed detector 62 detects light in three wavelength ranges. In the illustrated exemplary embodiment, however, only a partial spectrum from the red spectral range corresponding to the wavelength of the laser light is used for the measurement. Both figures show the intensity on the ordinate and the location on the abscissa along a line of the two-dimensional detector. Since the detector is operated with 8-bit resolution, the ordinate has $2^8=256$ steps of intensity. The two-dimensional image of the detector is additionally shown, the intensity being coded in gray levels.

As is clear from FIG. 6, a considerable light intensity is transmitted by the second waveguide 4 so that the intensity of the reference signal reaches the saturation intensity in several pixels.

Due to the presence of particles with a diameter of 140 nm and a refractive index of 1.4 on the functionalized layer in the interruptions 3 of the first measuring point 25 of the first waveguide 2, the red light is scattered to such an extent that the intensity decreases by a factor of more than 5. As a result of differential measurement or comparison of the reference signal shown in FIG. 6 with the measurement signal shown in FIG. 7, the presence of the particles can be clearly detected and quantified.

It should be noted that the second waveguide 4 for the generation of the reference signal is optional and can also be omitted in some embodiments of the invention. In this case, the measurement signal and the reference signal can also be detected sequentially by means of a single waveguide and/or the measurement signal can be evaluated by means of calibration data from a database.

Of course, the invention is not limited to the illustrated embodiments. Therefore, the above description should not be regarded as restrictive but as explanatory. The following claims are to be understood in such a way that a stated feature is present in at least one embodiment of the invention. This does not exclude the presence of further features. If the claims and the above description define "first" and "second" embodiments, this designation is used to distinguish between two similar embodiments without determining a ranking order.

What is claimed is:

1. An optical sensor comprising
a substrate having a first side and an opposite second side which are connected to each other by lateral edges, the first and second sides being the largest surfaces of the substrate,
at least one first waveguide arranged on the first side, the first waveguide having at least one first measuring point, the first measuring point comprising at least one interruption of the first waveguide,
a second waveguide arranged on the first side, the second waveguide having at least one second measuring point, the second measuring point comprising at least one interruption of the second waveguide,
a third waveguide having a first end and an opposite second end,
wherein:
the first and second waveguides are spaced apart from one another on the first side, each of the first waveguide and the second waveguide having a first end and an opposite second end, the first and second ends of each of the first waveguide and the second waveguide terminate at one of the lateral edges of the substrate,
the first measuring point is functionalized by at least one coating,
the second measuring point is not functionalized by at least one coating,
the second end of the third waveguide is adapted to be coupled to a detector;
the first end of the third waveguide is arranged adjacent to the first measuring point; and
the first end of the third waveguide is adapted to receive at least a part of scattered light originating from the first measuring point.

2. The sensor according to claim 1, wherein any of the first or second measuring point has at least 3 interruptions of the first waveguide and up to 60 interruptions of the first or second waveguide.

3. The sensor according to claim 1, wherein any of the first or second measuring point has at least 50 interruptions of the first waveguide and up to 100 interruptions of the first or second waveguide.

4. The sensor according to claim 2, wherein the interruptions of the respective waveguide in any of the first or second measuring points are arranged periodically.

5. The sensor according to claim 2, wherein the interruptions of the respective waveguide in any of the first or second measuring points have a length from about 2 µm up to about 20 µm.

6. The sensor according to claim 1, wherein:
at least one first coupler is arranged on the substrate, said first coupler being in a light guiding arrangement with the first end of any of said waveguides; and
at least one second coupler is arranged on the substrate, said second coupler being in a light guiding arrangement with the second end of any of said waveguides.

7. The sensor according to claim 6, further comprising at least one light source and at least one detector, wherein the light source is connected to any of said first couplers and the detector is connected to any of said second couplers.

8. The sensor according to claim 1, wherein the substrate comprises any of a glass or a polymer or a semiconductor.

9. The sensor according to claim 1, further comprising:
at least one fourth waveguide having a first end and an opposite second end, wherein:
the second end of the fourth waveguide is adapted to be coupled to a detector;
the first end of the fourth waveguide is arranged adjacent to the first measuring point; and
the first end of the fourth waveguide is adapted to receive at least a part of scattered light originating from the second measuring point.

10. A method for detecting pathogenic germs, comprising:
providing an optical sensor in accordance with claim 1;
applying a liquid sample comprising pathogenic germs to at least the first measuring point;
coupling an optical signal into at least a first end of the first waveguide; and
determining an intensity of the optical signal at a second end of the first waveguide.

11. The method according to claim 10, wherein the optical signal has a single wavelength.

12. The method according to claim 10, wherein the optical signal has a plurality of wavelengths and the intensity of the optical signal exiting from the second end is determined at a plurality of wavelengths.

13. The method according to claim 10, wherein applying a liquid sample comprising pathogenic germs includes:

applying a predetermined amount of the liquid sample to the first measuring point;
applying a predetermined amount of the liquid sample to the second measuring point;
waiting for a predetermined period of time;
washing off the liquid samples from the first and second measuring points, with a solvent; and
applying a reference liquid to at least one of the first and second measuring points.

14. The method according to claim 10, further comprising:
coupling an optical signal into a first end of the second waveguide; and
determining an intensity of the optical signal at the second end of the second waveguide; and
using the intensity of the optical signal at the second end of the second waveguide as a reference signal.

15. The method according to claim 10, further comprising:
coupling an optical signal into the first end of the second waveguide; and
determining intensities of the optical signals at the second ends of the first and second waveguides differentially.

16. The method according to claim 11, wherein:
the sensor further comprises at least one fourth waveguide having a first end and an opposite second end;
the second end of the fourth waveguide is coupled to a detector; and
the first end of the fourth waveguide receives at least a portion of scattered light originating from the second measuring point.

17. A system comprising a sensor according to claim 1 coupled to either a cell phone or to a tablet computer.

18. The system according to claim 17, wherein the sensor is a disposable, single-use article.

19. The system according to claim 17, wherein:
the cell phone or tablet computer comprises a camera and a light source;
an adaptor is mounted on the cell phone or tablet computer; and
the sensor is mounted to the adaptor such that the first ends of the first and second waveguides are opposed to the light source, and the second ends of the first and second waveguides are opposed to the camera.

20. The system according to claim 19, wherein:
the adaptor comprises a recess;
the sensor is housed in a sensor housing;
and the sensor housing is mounted in the recess of the adaptor.

21. An optical sensor comprising
a substrate having a first side and an opposite second side which are connected to each other by lateral edges, the first and second sides being the largest surfaces of the substrate,
at least one first waveguide arranged on the first side, the first waveguide having at least one first measuring point, the first measuring point comprising at least one interruption of the first waveguide,
a second waveguide arranged on the first side, the second waveguide having at least one second measuring point, the second measuring point comprising at least one interruption of the second waveguide,
a third waveguide having a first end and an opposite second end,
wherein:
the first and second waveguides are spaced apart from one another on the first side, each of the first wave guide and the second waveguide having a first end and an opposite second end, the first and second ends of each of the first waveguide and the second waveguide terminate at one of the lateral edges of the substrate,
the first measuring point is functionalized by at least one coating,
the second measuring point is not functionalized by at least one coating,
the second end of the third waveguide is adapted to be coupled to a detector;
the first end of the third waveguide is arranged adjacent to the first measuring point; and
the first end of the third waveguide is adapted to receive at least a part of scattered light originating from the second measuring point.

* * * * *